(12) United States Patent
Von Schuckmann

(10) Patent No.: US 9,956,361 B2
(45) Date of Patent: May 1, 2018

(54) DEVICE FOR THE PORTIONED OUTPUT OF MEDICATION

(71) Applicant: Alfred Von Schuckmann, Kevelaer (DE)

(72) Inventor: Alfred Von Schuckmann, Kevelaer (DE)

( * ) Notice: Subject to any disclaimer, the term of this patent is extended or adjusted under 35 U.S.C. 154(b) by 708 days.

(21) Appl. No.: 14/386,283

(22) PCT Filed: Apr. 2, 2013

(86) PCT No.: PCT/EP2013/056927
§ 371 (c)(1),
(2) Date: Sep. 18, 2014

(87) PCT Pub. No.: WO2013/150021
PCT Pub. Date: Oct. 10, 2013

(65) Prior Publication Data
US 2015/0114393 A1   Apr. 30, 2015

(30) Foreign Application Priority Data

Apr. 5, 2012 (DE) .................. 10 2012 102 974
Jun. 5, 2012 (DE) .................. 10 2012 104 850

(51) Int. Cl.
*A61M 15/00* (2006.01)

(52) U.S. Cl.
CPC ...... *A61M 15/0051* (2014.02); *A61M 15/005* (2014.02); *A61M 15/0023* (2014.02);
(Continued)

(58) Field of Classification Search
CPC .......... A61M 15/0045; A61M 15/0046; A61M 15/0051; A61M 15/0055; A61M 15/00;
(Continued)

(56) References Cited

U.S. PATENT DOCUMENTS 5,582,162 A   12/1996 Petersson
5,590,645 A    1/1997 Davies et al.
(Continued)

FOREIGN PATENT DOCUMENTS

| DE | 41 06 379 A1 | 9/1991 | |
| FR | 2 961 186 A1 | 12/2011 | |
| WO | WO 2012012827 A1 * | 2/2012 | ........ A61M 15/0045 |

OTHER PUBLICATIONS

International Search Report of PCT/EP2013/056927, dated Jul. 10, 2013.

*Primary Examiner* — Tan-Uyen (Jackie) T Ho
*Assistant Examiner* — Joseph D Boecker
(74) *Attorney, Agent, or Firm* — Collard & Roe, P.C.

(57) ABSTRACT

A device outputs portioned medications (M) from individual chambers of a strip arranged one behind the other. The strip includes a base strip and a closure strip and the raised chambers of the strip can be opened by pressing a handle by sharp-edged deflection of the closure strip. In order to simplify the design and for safe operation, a chamber elevation directed toward the mouthpiece opening blocks the actuation of the handle using a blocking element, in which position a chamber arranged in front that has already been freed from the closure strip lies above a fall-through opening, which opening is closed using a flap that can be moved into the opening position by the suction air flow.

13 Claims, 16 Drawing Sheets

(52) U.S. Cl.
CPC .... *A61M 15/0043* (2014.02); *A61M 15/0045* (2013.01); *A61M 15/0055* (2014.02); *A61M 15/0026* (2014.02); *A61M 2202/064* (2013.01)

(58) Field of Classification Search
CPC .......... A61M 15/0001; A61M 15/0023; A61M 15/0043; A61M 15/005; A61M 15/0053
See application file for complete search history.

(56) References Cited

U.S. PATENT DOCUMENTS

| | | | | |
|---|---|---|---|---|
| 5,692,496 | A * | 12/1997 | Casper | A61M 15/0028 128/200.24 |
| 5,860,419 | A | 1/1999 | Davies et al. | |
| 5,873,360 | A | 2/1999 | Davies et al. | |
| 6,032,666 | A | 3/2000 | Davies et al. | |
| 6,722,363 | B1 * | 4/2004 | Von Schuckmann | A61M 15/0045 128/203.15 |
| 7,231,920 | B2 * | 6/2007 | Harvey | A61M 15/0045 128/202.22 |
| 2003/0172927 | A1 * | 9/2003 | Young | A61M 15/0045 128/203.15 |
| 2004/0244794 | A1 * | 12/2004 | Richards | A61K 9/0075 128/203.15 |
| 2005/0258182 | A1 * | 11/2005 | Anderson | A61M 15/0045 221/7 |
| 2006/0102511 | A1 * | 5/2006 | Pasbrig | A61M 15/0045 206/531 |
| 2006/0196504 | A1 * | 9/2006 | Augustyn | A61M 15/0045 128/203.15 |
| 2008/0223366 | A1 * | 9/2008 | Davies | A61M 15/0045 128/203.15 |
| 2009/0173345 | A1 * | 7/2009 | Wachtel | A61M 15/0045 128/203.12 |
| 2010/0288278 | A1 * | 11/2010 | Pocock | A61M 15/0045 128/203.21 |
| 2011/0226244 | A1 * | 9/2011 | Perkins | A61M 15/0045 128/203.15 |
| 2013/0139815 | A1 | 6/2013 | Colomb et al. | |

* cited by examiner

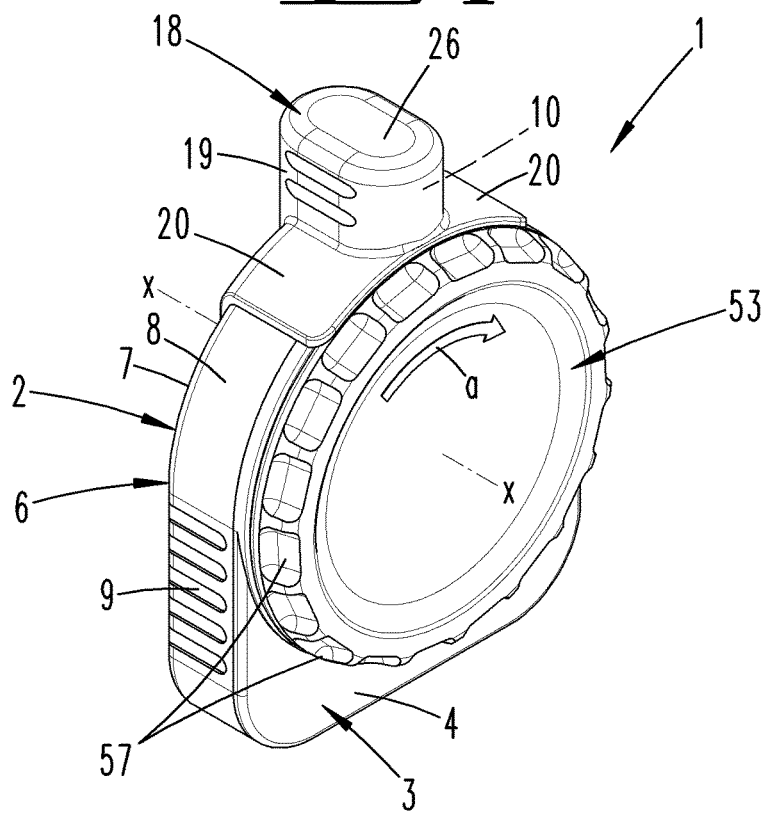
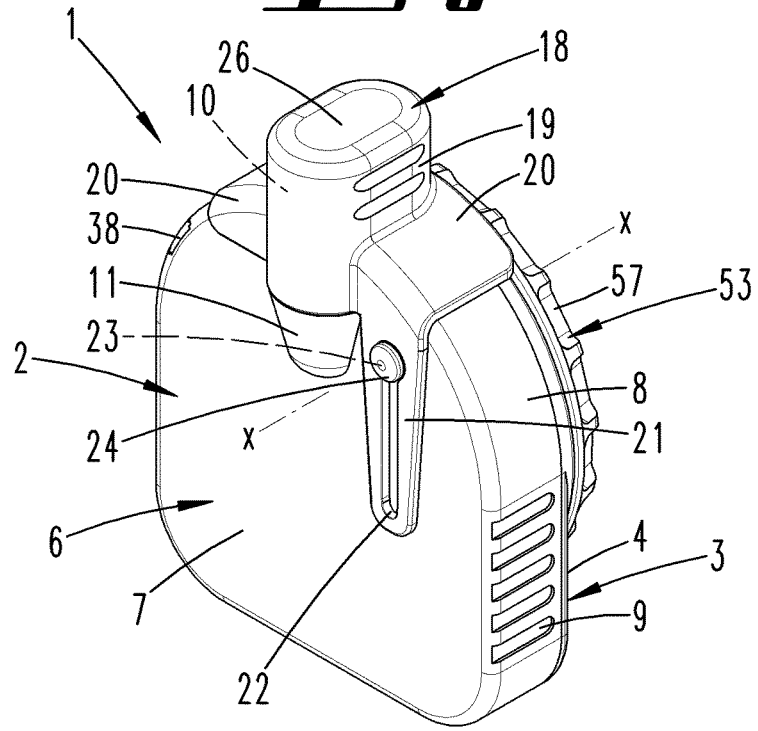

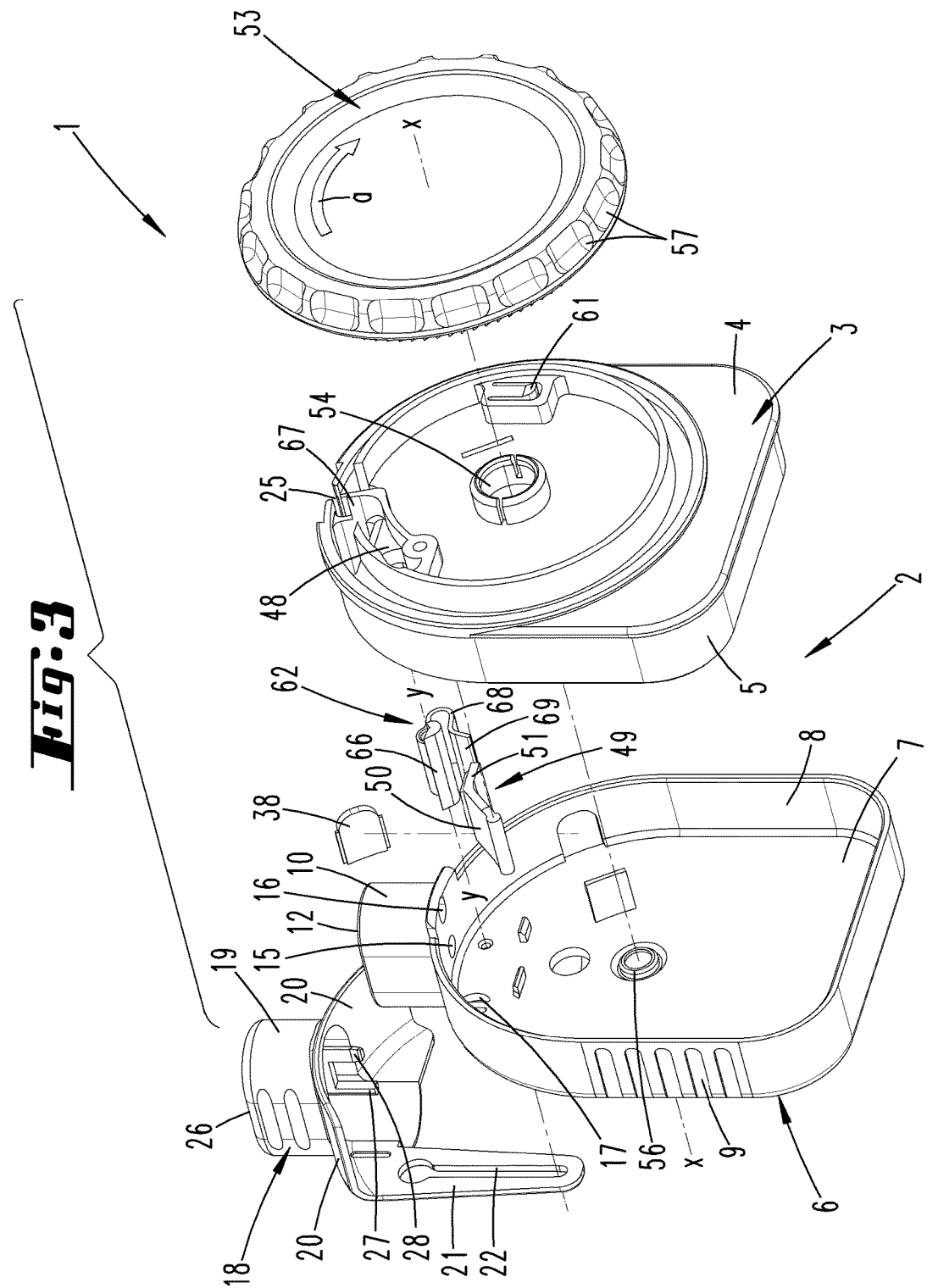

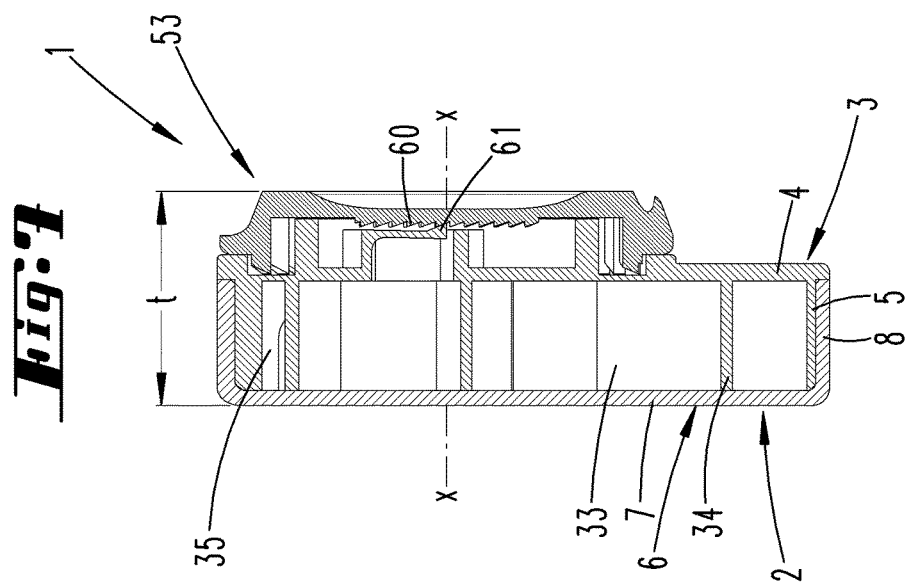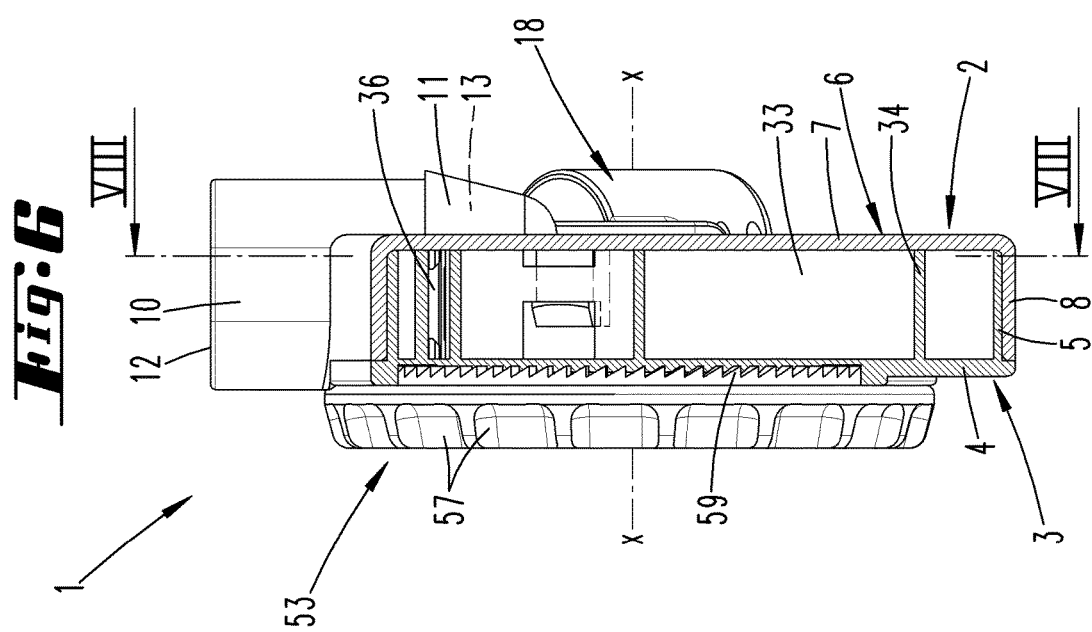

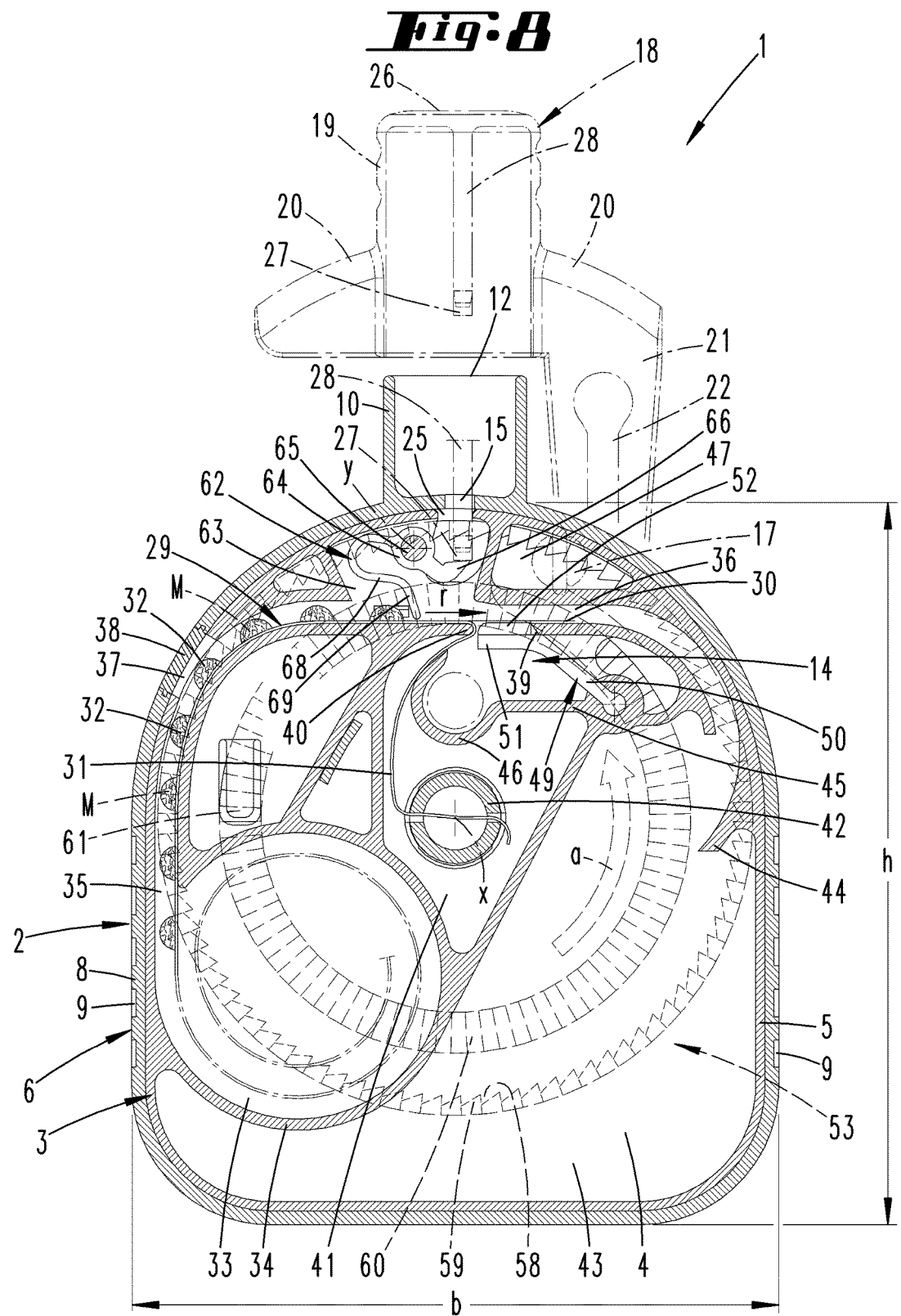

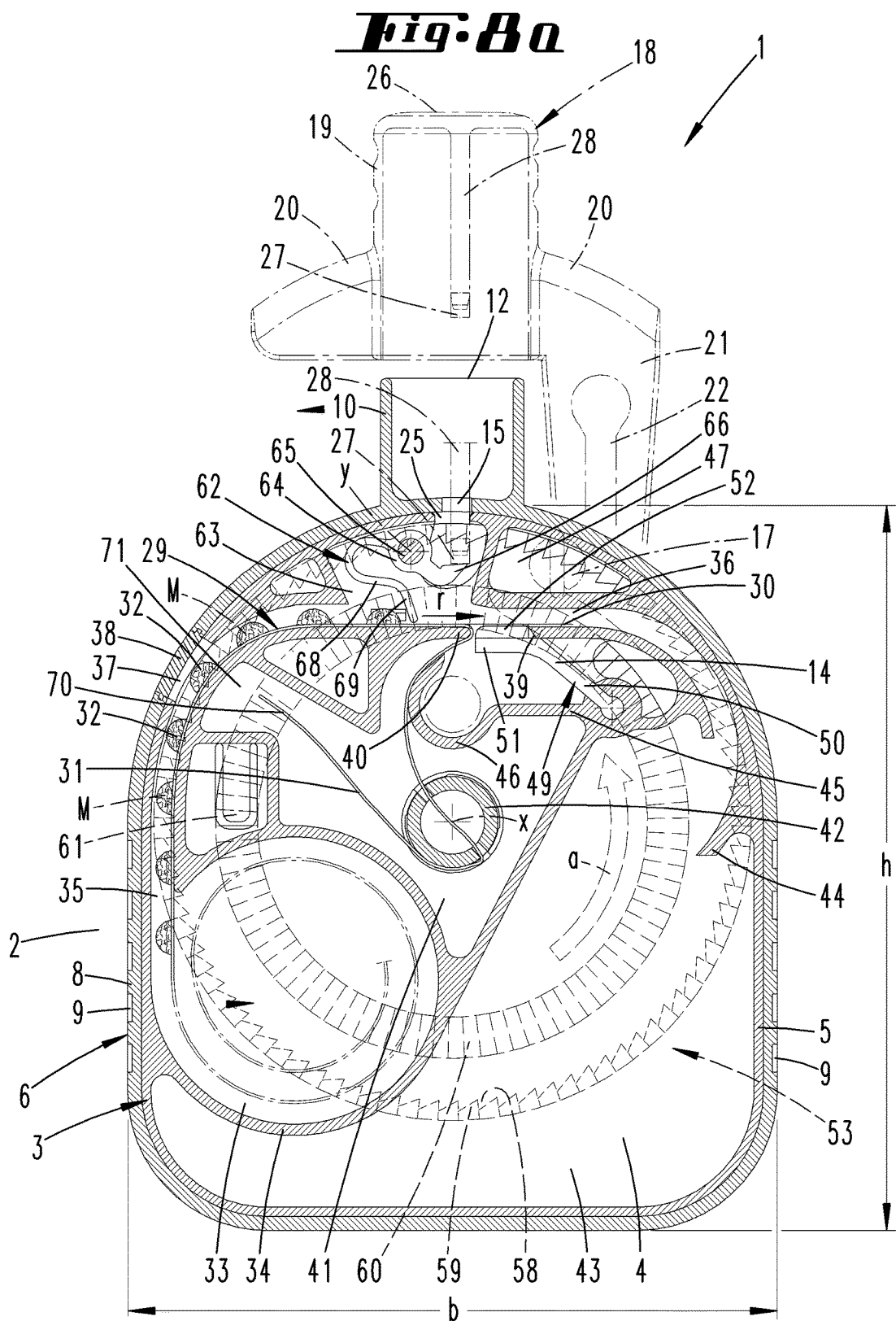

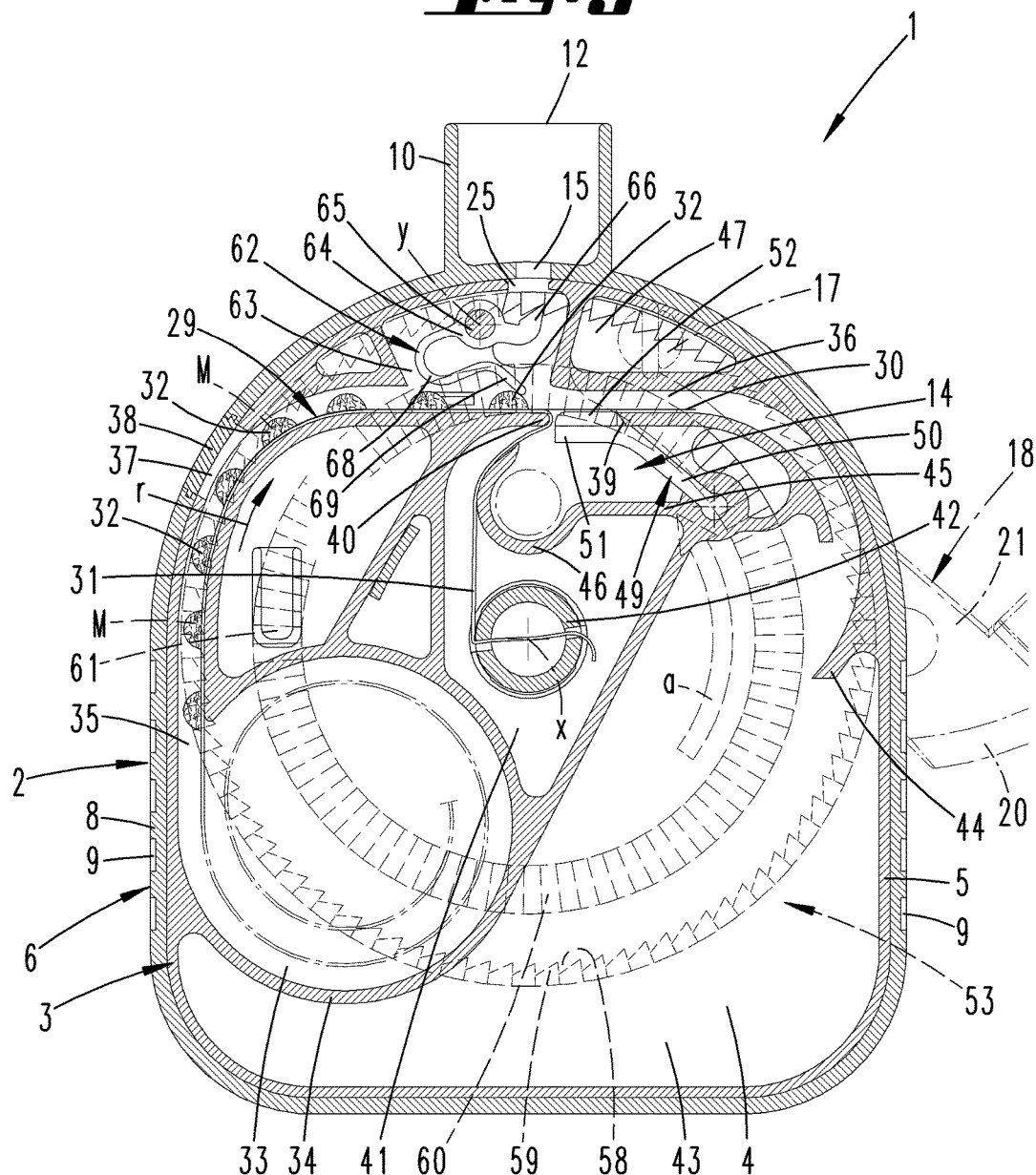

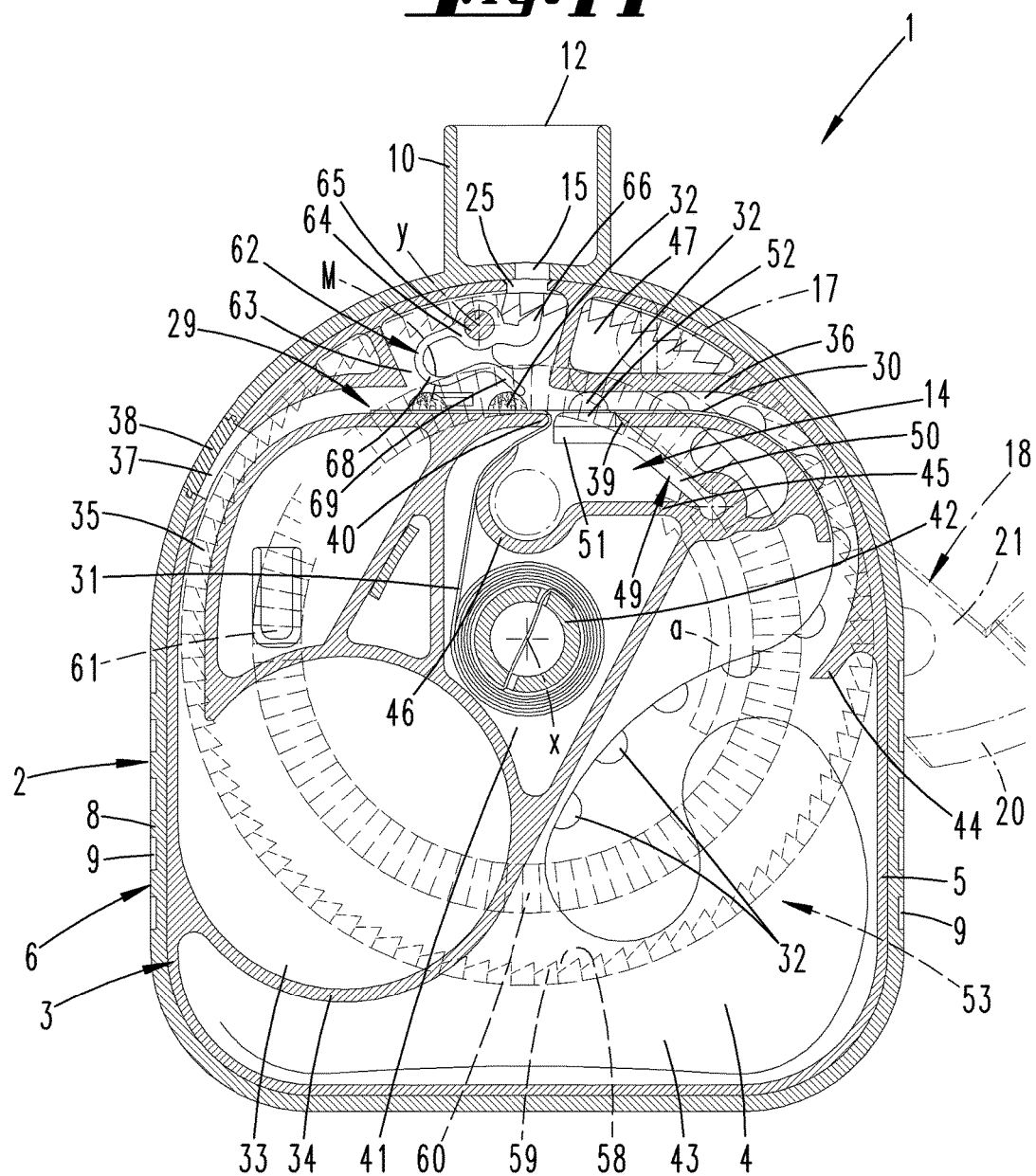

DEVICE FOR THE PORTIONED OUTPUT OF MEDICATION

CROSS REFERENCE TO RELATED APPLICATIONS

This application is the National Stage of PCT/EP2013/056927 filed on Apr. 2, 2013, which claims priority under 35 U.S.C. § 119 of Germany Application Nos. 10 2012 102 974.1 filed on Apr. 5, 2012, and 10 2012 104 850.9 filed on Jun. 5, 2012, the disclosures of which are incorporated by reference. The international application under PCT article 21(2) was not published in English.

The invention relates to a device for the portioned output of medication.

Devices of the type in question are known, for example from DE-OS 4106379. They are configured for the manually operable output of portioned medication, in particular inhalable, powdery medication. For this purpose, a transportable strip is provided in the device, said strip substantially consisting of a base strip, in which separate chambers that are uniformly spaced apart from one another in the strip-transporting direction are formed to receive portions of medication, and a closure strip, which seals the chambers filled with the medication and is suitable for being pulled off the base strip. The portioned medication stored in the chamber is freed for outputting, by the exposing of a chamber as a result of the pulling off of the closure strip. The chambers configured in the base strip are raised here in relation to the strip base, which, preferably configured to be flat, in particular on the side remote from the chamber elevation, provides the contact face for the closure strip.

With regard to the above-described prior art, a technical problem of the invention is regarded as being the provision of a device of the type in question, which can be actuated in a trouble-free manner in a simple construction and which can also cope with less robust strips.

One possible solution to the problem is provided according to a first inventive idea, whereby a chamber elevation directed towards the mouth piece opening blocks actuation of the handle by means of a blocking element, in which position one of the arranged upstream of the blocking chamber elevation in terms of movement and freed from the closure strip is located above a fall-through opening, which opening is closed by means of a flap which can be moved into the open position by the suction air stream. As a result of the pulling off of the closure strip from the base strip and the deflection of the closure strip, the chamber is freed for a subsequent, preferred emptying of the suction air by the user, almost by normal breathing. The chamber is opened on the underside. The content of the chamber undergoes an acceleration due to gravity in addition to the suction effect. The device is most suitable for holding above the head. A precise position for the chamber to be emptied is preferably provided by the blocking element for the rotary handle, in which blocking position the chamber arranged upstream of the controlling chamber in terms of movement is freed, by deflecting the closure strip, to empty the suction air via the fall-through chamber. The amount of displacement of the strip for providing a next, filled chamber is preferably directly tapped at the chambers, in that the blocking element provided is moved across the chambers rising above the strip base of the strip or the base strip. The amount of spacing of two chambers located one behind the other in the movement direction of the strip is accordingly immediately used as the amount for the displacement of the strip, to provide the next, filled chamber. This further provides the advantage that various base strips with different spacings or a base strip with different chamber spacings of the successive chambers in the movement direction can also be used in the device if required. In order to counteract the portion of medication falling out due to gravity into the output region of the device, through which suction air can flow, before the inhalation has been carried out, this chamber freed with respect to the closure strip is firstly closed by the flap. Only when the suction air flow starts as a result of an inhalation process carried out by the user is the flap moved, preferably pivotally displaced, into a position that simultaneously frees the fall-through opening on the device side and therefore the chamber opening, after which the portion of medication trickles out of the chamber into the output and flow region, preferably assisted by gravity, and is transported by the prevailing suction air flow for inhalation. The clearing of the chamber is more preferably assisted here by the swirling of suction air guided through the chamber. The flap is more preferably preloaded, in particular spring-preloaded, into the position closing the fall-through opening. This preloading results in a preferred configuration, only or at least for the major part, by means of the material of the flap itself, which is produced from a rubbery-elastic material in a further preferred configuration. In particular, a substantially pliable flap is provided here, the restoring force of which resulting from the resilience, preferably only being able to be overcome by the suction air flow prevailing in the course of the inhalation. As an alternative, for example, a flap that is rigid per se and which further, for example, is loaded by a separate spring, such as, for example, a leg spring or compression spring, is provided. As a result of the arrangement of a flap of this type, it is ensured that the medication is only output into the output chamber, through which suction air can flow, at the time at which the inhalation actually occurs. Moreover, a, for example, double portioning is advantageously counteracted by this.

Further features of the invention will be described below, also in the description of the figures, often in their preferred association with the device according to an embodiment of the invention or with features of other embodiments. However, they may also be significant if associated with only individual features of the device according to an embodiment of the invention, or of the relevant other embodiment or independently, in each case.

It is thus provided in a more preferred configuration that the closure strip has an initial stop position, shortly before the front chamber reaches the deflection edge and before the subsequent chamber actuates the blocking element. This initial stop position is preferably the delivery position of the device. Here, the front chamber is located in a position at a distance from the fall-through opening in particular, and also in particular in a position at a distance from the deflection edge. Furthermore, in this initial position the chamber is sealed closed by the closure strip. Viewed in the movement direction of the strip, the distance between two chambers, in particular between the first and second chambers in the movement direction, is adjusted to the attainment of this initial stop position in particular.

In addition it is preferred for the strip with the closed chambers to be wound-on in a winding chamber and for the base strip continuing beyond the deflection point to be inserted into an enlarged insertion chamber, while the closure strip winds-on on a mandrel driven by the rotary handle. Accordingly, only one winding device that can be actively rotated by the rotary handle is preferably provided, namely more preferably, the mandrel to wind-on the closure strip pulled off from the base strip.

One configuration that is particularly structurally favourable, and even more favourable with regard to the overall dimensions of the device, provides that the mandrel extends between the winding chamber and the insertion chamber. The nesting of the winding chamber, insertion chamber and a closure strip winding chamber having the mandrel are virtually provided here in terms of the outline, in an outline area preferably extending perpendicular to the rotational axis of the mandrel.

It is further preferred in this context for the blocking element, the fall-through opening and the mandrel to be located one behind the other substantially on a radial of the rotary handle or the rotational axis, more particularly in an angle range of 0° to 30°, more preferably 0° to 15°, extending radially from the mandrel axis.

The device has a stepping mechanism for the targeted further displacement of the strip, the blocking element preferably being part of this stepping mechanism. The blocking element is displaced into a position in particular blocking the rotary handle in the cooperation position, in which the blocking element encounters the elevation of a chamber connected downstream in the movement direction of the outputting chamber. However, the blocking does not exert undue stress on the wall of the chamber elevation, because the bearing of the blocking element receives a load still exerted to some extent by the rotary handle. The sensing arm of the blocking element can also be resiliently movable. A two-armed blocking element is preferred in this context, one arm being configured for cooperation with the chamber elevation and the other arm being configured for cooperation with a serration of the rotary handle.

The rotary handle is preferably formed as a plate having a large surface area, which is arranged so as to overlap at least a portion of the surface of the side wall of the housing, in order to facilitate handling.

In order, in particular after inhalation has taken place, to cancel this blocking position of the rotary handle, to prepare the next inhalation, it is provided in a preferred configuration that the sensing blocking element can be returned from the projection of a mouth closure cap into the preparation position to sense the next chamber. Accordingly, the closure cap of the device to close the mouth nozzle surrounded by the lips during the inhalation is simultaneously a functional part for using the device. The closure cap is used to prepare the device for the next inhalation, in that the projection of the closure cap preferably either acts on the blocking member, by passing through the mouth nozzle or else running outside the mouth nozzle and passing through a corresponding housing wall, in such a way that the sensing portion of the blocking element is displaced into a position for preparing to sense the following chamber, this accompanying the cancellation of the blocking of the rotary handle by the blocking element.

Since the mouth closure cap in the preferred embodiment is simultaneously a functional part of the device, in particular of the stepping mechanism, this is more preferably permanently held on the device.

It is also preferable for the mouth closure cap to be longitudinally, displaceably and pivotally placeable on the mouth nozzle. The longitudinal displaceability allows the sliding, substantially linear placing of the cap onto the mouth nozzle, preferably surrounding and covering said nozzle in a cap-like manner, the projection of the closure cap preferably acting on the sensing blocking element to displace it into the unblocking position during this linear placing movement. The pivotability of the closure cap allows the user to displace said closure cap into a position that does not disturb the inhalation process, in particular the enclosing of the mouth nozzle with the lips.

In a further preferred configuration it is provided that the projection of the mouth closure cap blocks the rotary handle. Accordingly, in the mouth nozzle closure position, i.e. more preferably in the non-use position of the device, rotation of the handle and accompanying this, further displacement of the strip is prevented, this although the sensing blocking element is displaced by the further projection of the closure cap into a non-blocking position. The blocking projection of the closure cap preferably acts here on the same row of the toothed formation of the rotary handle or of a device element also entrained to rotate by the rotary handle, on which the blocking element is also configured to engage in the use position of the device. The blocking of the rotary handle also allows this handle to be made very large and thus also operable by children.

An introduction portion pointing in the direction of the insertion chamber is preferably also provided. Said introduction portion is preferably located upstream of the insertion chamber in the movement direction of the base strip, more preferably forming the entry region of said insertion chamber.

In a preferred configuration, the introduction portion is formed ramp-like for the further preferred deflection of the base strip into a region of the insertion chamber remote from the introduction portion. The stack-like depositing of the base strip in the insertion chamber is advantageously assisted thereby.

The ranges or value ranges or multiple ranges disclosed above and below also include all the intermediate values with respect to the disclosure, in particular in $\frac{1}{10}$ steps of the respective dimension, thus optionally also without dimension, in particular 1.01 times etc., on the one hand, to delimit the range limits mentioned from below and/or above, but also alternatively or additionally with regard to the disclosure of one or more singular values from the respective range given.

The suction air stream, deflected a multiple times, promotes mixing.

The invention will be described below with the aid of the accompanying drawings, which, however, only show one embodiment (embodiments). A part which is described only in relation to one of the embodiments and which has not (exactly) been replaced by another part in a further embodiment due to the special feature exposed therein is thus also described for this further embodiment as a part which may in any case be present. In the drawings:

FIG. 1 shows a device of the type in question in a perspective view with a view of a front side having a rotary handle, relating to a non-use position of the device;

FIG. 2 shows a view corresponding to FIG. 1, but with a view of the rear;

FIG. 3 shows an exploded perspective view of the device;

FIG. 6 shows the section along the line VI-VI in FIG. 5;

FIG. 7 shows the section along the line VII-VII in FIG. 5;

FIG. 8 shows the section along the line VIII-VIII in FIG. 6, with the closure cap represented by a dash-dot type of line, both in the closure position and in the raised position freeing the mouth nozzle, further relating to the base position of the device before a first use;

FIG. 8a shows a view corresponding to FIG. 8, relating to an alternative embodiment;

FIG. 9 shows a view corresponding to FIG. 8, but in the course of the actuation of the rotary handle, to displace a strip provided in the device;

FIG. 17 shows a sectional view corresponding to FIG. 11, relating to a position after the carrying out of a plurality of portioned outputs of medication.

Figure 4:
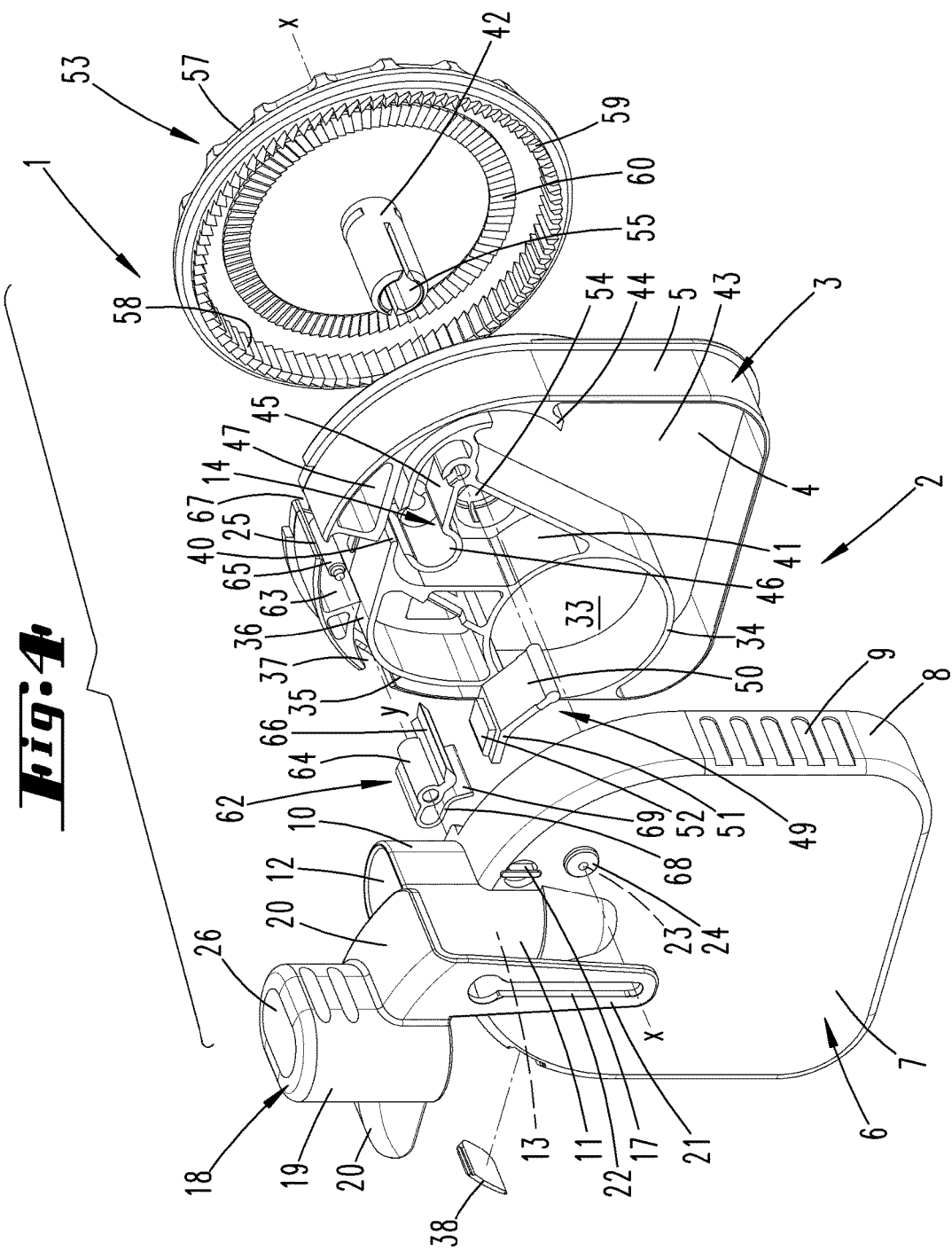
FIG. 4 shows a further exploded perspective view of the device.

The whole device 1 for the portioned output of medication, in particular inhalable, powdery medication is firstly shown and described in relation to FIGS. 1 and 2.

The device 1 can be handled by the user, more preferably with dimensions of the device that are favourable to handling. A width b is thus provided, viewed over the outline of the device 1 according to the view in FIG. 8, which preferably corresponds to 0.7 to 1.2 times, more preferably 0.9 to 1 times, the height h of the device 1 viewed perpendicular thereto (not taking into consideration a mouth piece connecting piece). The depth t of the device 1 viewed transversely to this preferably corresponds to 0.15 to 0.5 times, more preferably 0.2 to 0.3 times, the height h.

Accordingly, the device 1 is present in a size allowing it to be carried close to the body, for example in the pockets of clothing items.

The device 1 firstly has a housing 2. This is substantially in two parts.

A shell-like housing part 3 is firstly preferably provided, with a housing base 4 extending over the width b and the height h and a peripheral housing wall 5 extending substantially along the edge of the housing base 4 perpendicular thereto.

A housing lid 6 forming the second part of the housing 2 preferably engages over the housing part 3. Said lid has a housing cover 7, which is preferably oriented parallel to the housing base 4 of the one housing part 3 and from which, proceeding peripherally, a lid wall 8 is formed, extending perpendicular to the housing cover 7. The lid wall 8 peripherally encloses the housing wall 5 of the housing part 3, the inwardly pointing face of the lid wall 8 more preferably being supported on the free, peripheral edge of the housing wall 5 of the housing part 3.

Gripping zones 9, which are configured on the outside of the wall by regular indentations and elevations and which provide the secure engagement of the device 1, in particular when it is used, are formed in the region of the two lid wall portions extending in the height direction.

A mouth nozzle 10 centrally receiving a vertical passing centrally—in relation to the width b—through the housing 2 is further formed on the housing lid 6.

In an outline viewed in a projection onto the housing base extending over the width b, the mouth nozzle 10 is configured in such a way that a slot-like mouth face is produced in the width direction of the housing 2. In this case, the mouth nozzle 10 extends substantially proceeding from the housing base 4 of the one housing part 3 to above the plane of the housing cover 7 of the housing lid 6, in which region projecting above the housing cover 7 the mouth nozzle 10 passes into a funnel 11 formed to the side of the housing cover 7.

Proceeding from the portions of the housing wall 5 and lid wall 8 opposing one another in parallel, the housing wall 5 and lid wall 8 preferably extend in a section of a circle shape, with an arrangement of the mouth nozzle 10 in the zenith region of the curvature.

The mouth opening 12 encompassed by the wall of the mouth nozzle 10 preferably passes into a flow channel 13 limited by the funnel 11 and the associated wall portion of the lid wall 8 and running substantially parallel to a vertical passing through the device 1. Said flow channel preferably opens on the foot side, i.e. remote from the mouth opening 12, passing through the housing cover 7 in an output region 14 formed in the housing 2.

The base of the mouth nozzle 10 formed by the lid wall 8 has two through-openings 15 and 16 one behind the other in the width direction of the housing 2 and distanced from one another.

Furthermore, an inflow opening 17 passing through the housing cover 7 is furthermore provided in the housing cover 7 laterally next to the formed funnel 11.

When the device 1 is not being used, the mouth nozzle 10 is covered with a mouth closure cap 18. The latter firstly has a pot-like slip-over portion 19 which substantially completely encompasses the mouth nozzle 10 and at least a part portion of the funnel 11, spans the mouth opening 12 and which, in the closure position of the device according to FIG. 1, passes on both sides into wing-like portions 20 for support on the associated surface of the lid wall 8.

A strip-like guide portion 21, which rests at least virtually flat on the facing surface of the lid wall 8, extends—preferably in a parallel orientation to a perpendicular through the housing 2—from the portion 20 facing the inflow opening 17 in the lid wall 8 in the closure position.

The guide portion 21 is preferably provided with a slot-like recess 22 extending virtually over the entire length thereof. A journal 23, which is raised perpendicularly from the lid wall 8, preferably integral with the lid wall 8 and formed of the same material and which widens in relation to the root region in the housing cover 7 in a radially enlarged collar portion 24, engages in said recess to engage over the edges of the recess 22 running in parallel.

Figure 5:
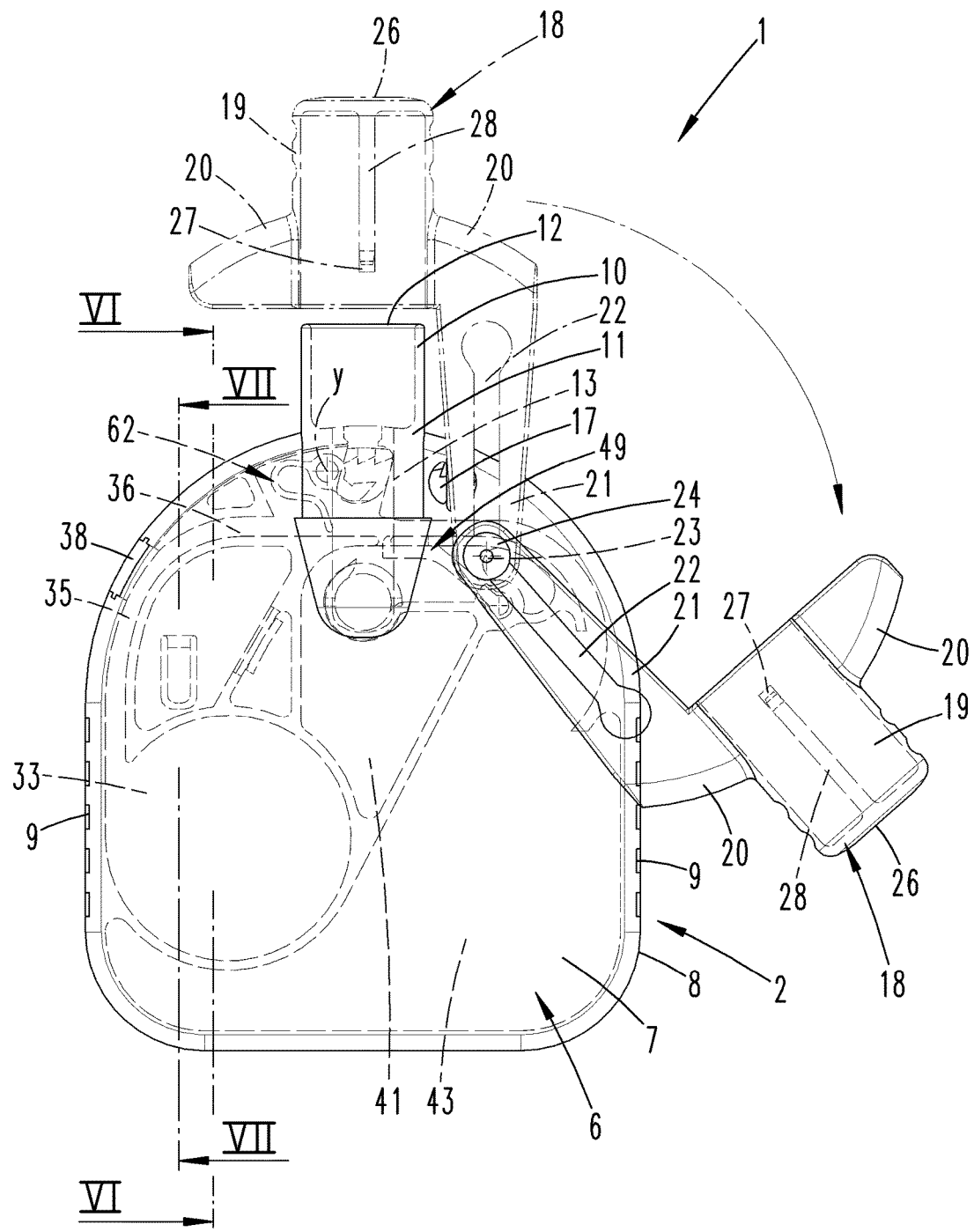
FIG. 5 shows the device in a view with the mouth closure cap lifted and pivoted from a mouth nozzle.
Figure 10:
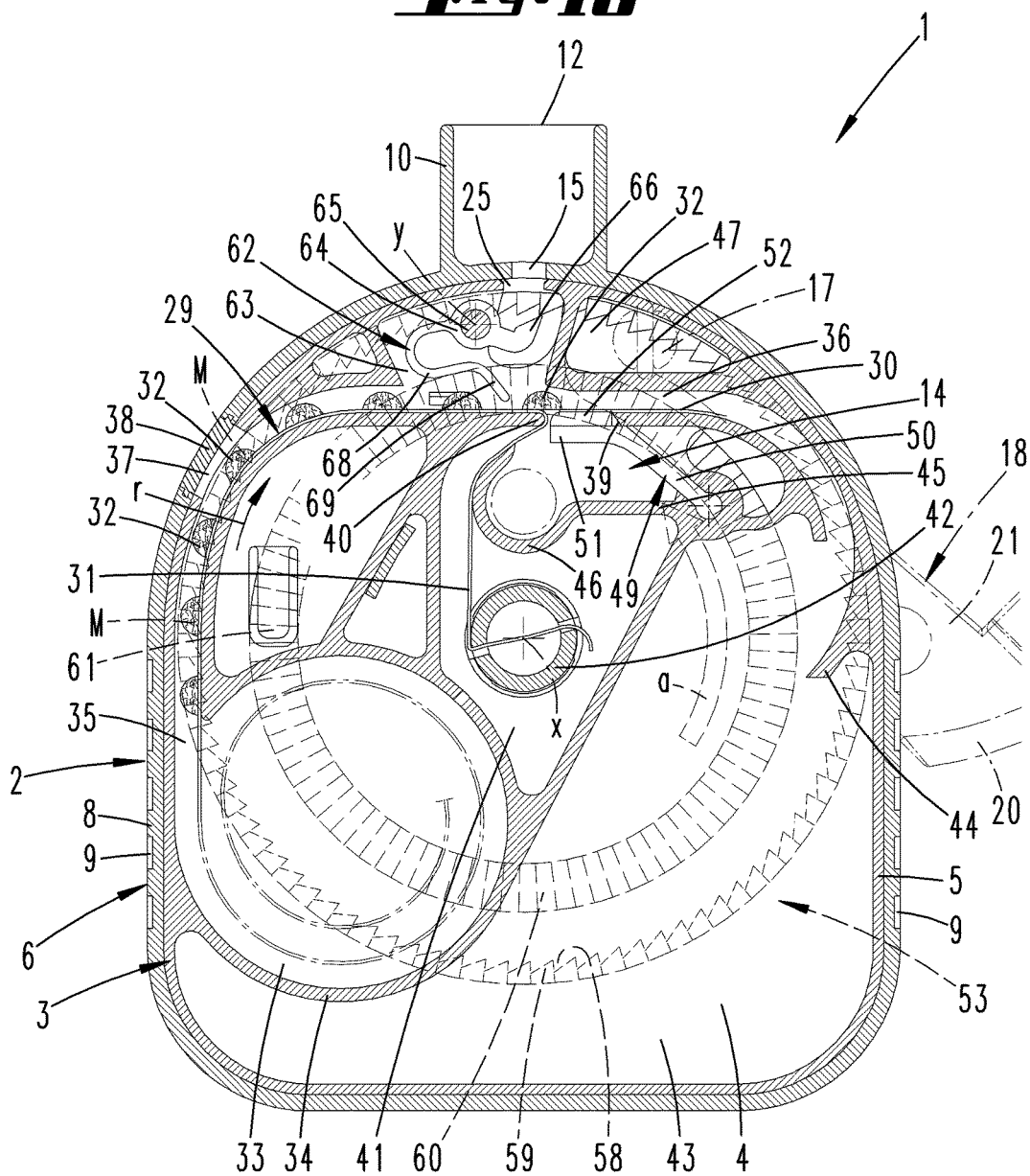
FIG. 10 shows a following view with respect to FIG. 9.
Figure 11:
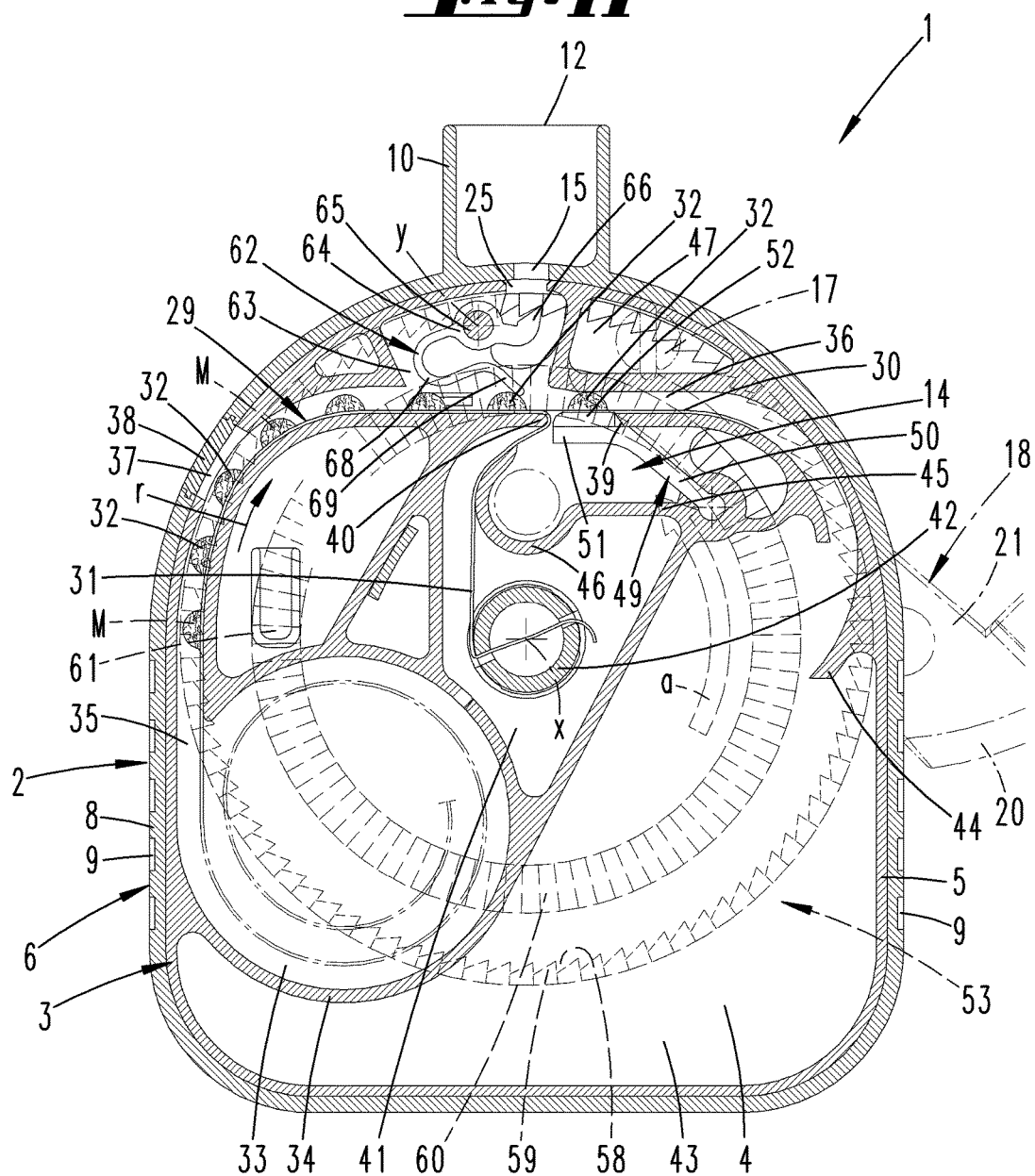
FIG. 11 shows a further following view of FIG. 10, relating to a displacement end position limited by a stop.
Figure 12:
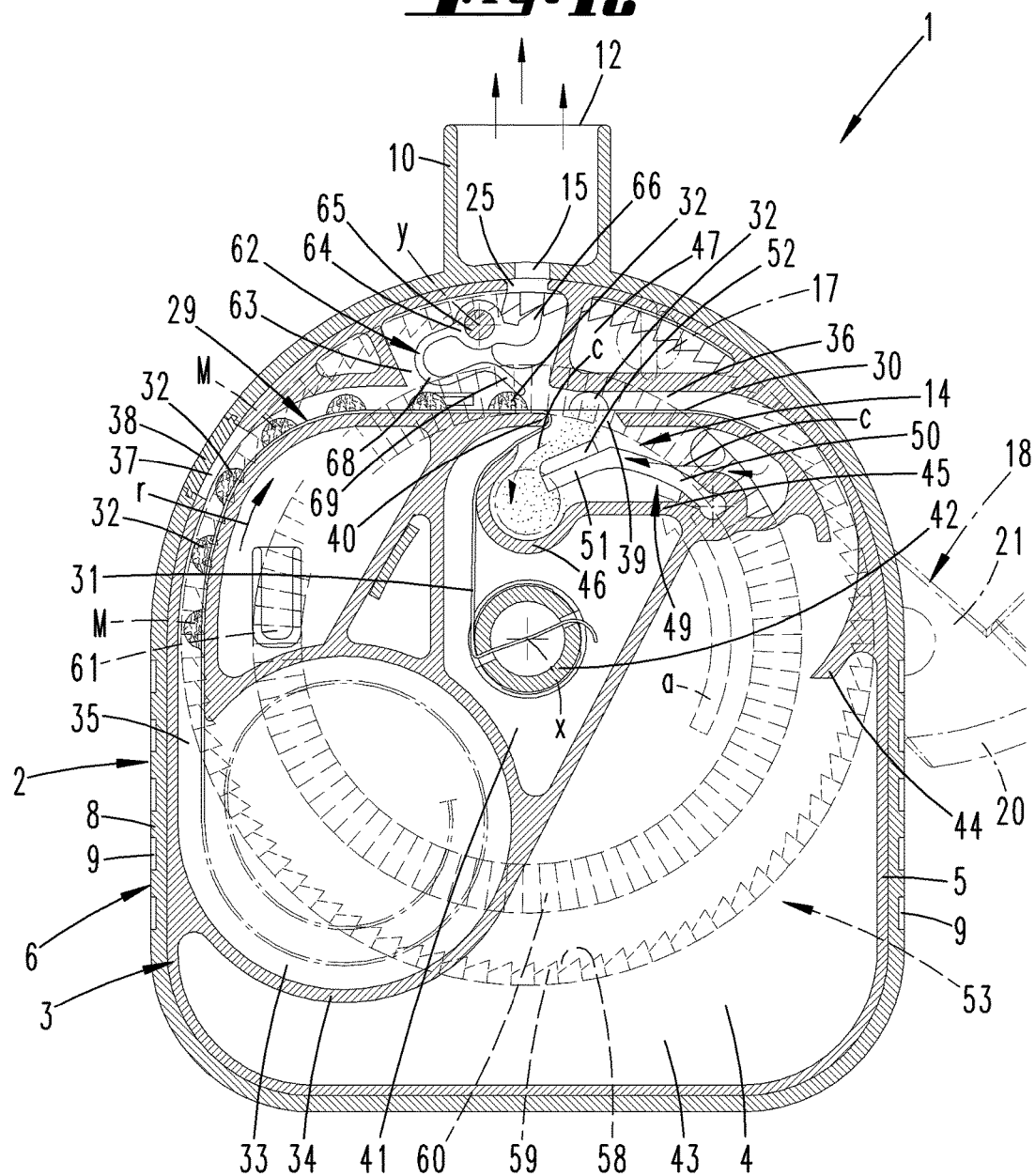
FIG. 12 shows a view corresponding to FIG. 11, but in the course of the inhalation process and use accompanying this of the suction air flow to empty a freed chamber storing a medication.
Figure 13:
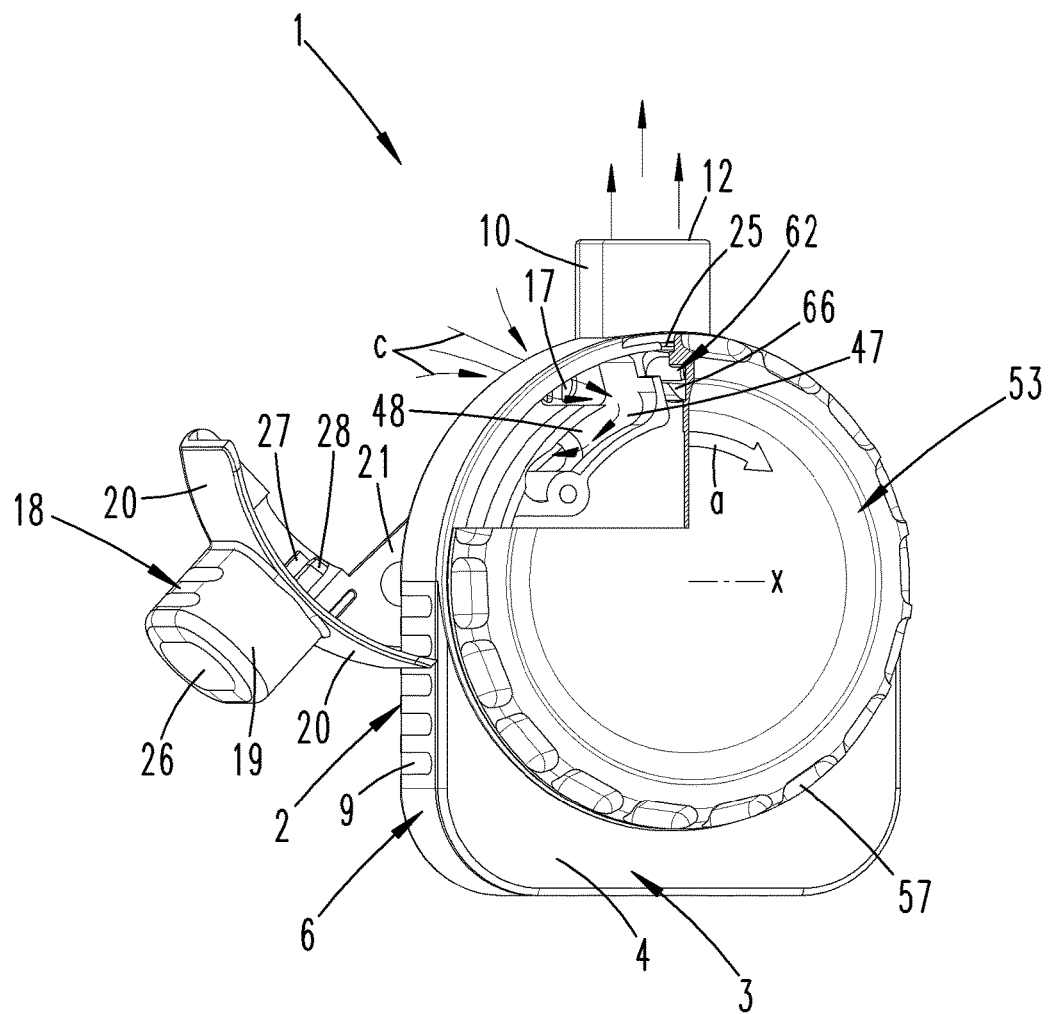
FIG. 13 shows a partially sectional perspective view according to the view in FIG. 1, showing the suction air flow path during inhalation.
Figure 14:
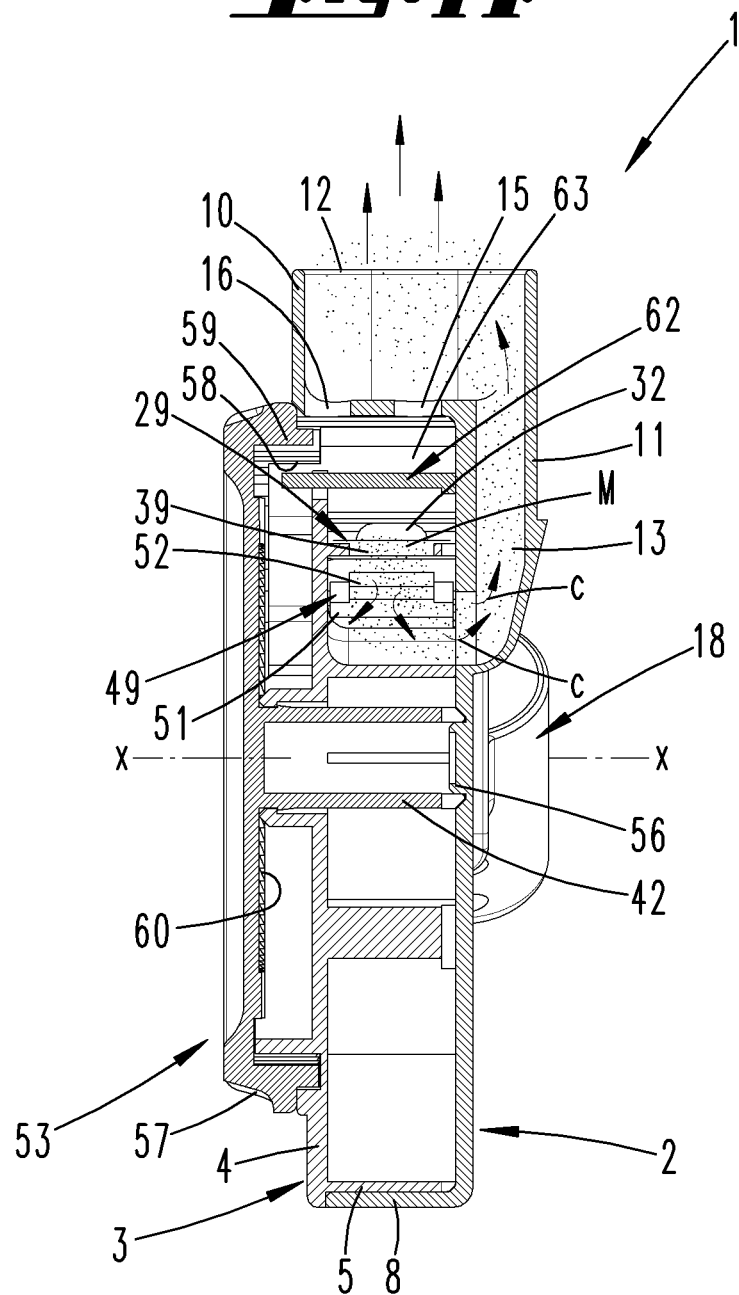
FIG. 14 shows a vertical sectional view through the device to further show the suction air flow path during inhalation.

As a result of this configuration, the mouth closure cap 18 is permanently held on the housing 2, thus longitudinally displaceably in the placing or pull-off direction of the closure cap in relation to the mouth nozzle 10 as well as pivotally about the journal 23 into a lateral position pivoted with respect to the mouth nozzle 10, according to FIG. 5. In this pivoted away position, the mouth closure cap 18 is preferably supported by an edge region of the portion 20 facing the guide portion 21 on the facing face of the lid wall 8.

Proceeding from the cap cover 26 of the slip-over portion 19 spanning the mouth opening 12 in the closure position, two projections 27, 28, which are positioned in such a way and selected with respect to their length so that they pass through the through-openings 15 and 16 in the region of the base of the mouth nozzle 10, extend substantially perpendicularly downward.

The housing wall 5 of the housing part 3 is interrupted below the through-opening 15 in the region of the lid wall 8, to form an engage-through slot 25.

A strip 29 is received in the housing 2. This is preferably an elongated strip with a length, which corresponds to 20 to 40 times, more preferably 25 to 35 times, the width of the strip viewed perpendicular thereto. In a preferred configuration, the strip 29 has a width of 10 to 15 mm, more preferably 12 to 13 mm, and a length of 300 to 500 mm, more preferably about 400 mm, viewed perpendicular thereto.

The strip 29 is placed in the housing 2 in such a way that it extends with its width in the width direction of the housing 2.

The strip 29 consists substantially of the base strip 30 and closure strip 31 being of the same width and located one above the other, the base strip 30 preferably being a metal strip, while the closure strip 31 is preferably configured in the manner of a plastics material film and/or aluminium foil.

Chambers 32 rising remote from the closure strip 31 and directed towards the mouth piece opening in FIG. 8 are formed out of the base strip 30. These chambers are more preferably pressed out of the material of the base strip 30. Each chamber 32 in this case has a width, which preferably corresponds to 0.5 to 0.9 times the strip width, more preferably about 0.75 times.

In a preferred configuration, a chamber width of 6 to 10 mm, more preferably 8 mm, is provided. The length viewed perpendicular thereto of each chamber 32—in the longitudinal extent of the strip 29—preferably corresponds to 0.3 to 0.7 times, more preferably about 0.5 times the chamber width.

All the chambers 32 have the same receiving volume and are preferably filled with a powdery, inhalable medication M.

In the longitudinal extent direction of the strip 29, the chambers 32 are arranged uniformly spaced apart from one another, 40 to 100, preferably 50 to 70, in particular about 60 chambers 32 preferably being provided over the length of the strip 29.

The spacing of two chambers 32 located one behind the other—in relation to the longitudinal extent of the strip 29—approximately corresponds to the selected chamber width, more preferably 6 to 10 mm, in particular about 8 mm, more preferably corresponding to 0.5 to 0.9 times the strip width, preferably about 0.75 times the strip width.

The strip 29 is placed loosely wound-on in a winding chamber 33 configured between the housing base 4 and the lid wall 8.

The winding chamber 33 is substantially circular in outline, the wall 34 surrounding the winding chamber preferably being integral with the housing part 3 and formed of the same material. The winding chamber wall 34 preferably extends perpendicularly to the housing base 4.

More preferably, the winding chamber 33 is, in particular, associated with the portion of the housing wall 5 running linearly, which portion is remote from the inflow opening 17. The winding chamber interior preferably opens into a substantially tangentially outgoing slot guide 35, which, preferably running parallel to the facing housing wall 5, passes into a transversely directed slot-like guide portion 36, intersecting the portion of a circle-like region of the housing wall 5 in the manner of a secant, in an imaginary prolongation.

This guide portion 36 preferably extends parallel to a housing wall portion connecting the portions of the housing wall 5 oriented parallel to one another. The transition from the vertical slot guide 35 into the guide portion 36 that is horizontal viewed in relation to this is preferably rounded in such a way that the strip 29 guided over this region is, in particular, bend-free, but can moreover also preferably be guided with low friction.

The strip 29 is preferably placed in the slot guide 35 and the guide portion 36 in such a way that the elevations of the chambers 32 always point outwardly, i.e. substantially in the direction of the housing wall 5, the spacing of the walls, which run substantially parallel to one another and limit the slot guide 35 and the guide portion 36, being furthermore adapted to the height of the strip 29, viewed perpendicular to the width and longitudinal extent of the strip 29, so that the precise, even if also preferably low-friction, guidance of the strip 29 is provided thereby.

A window-like aperture 37, which, in the region of the lid wall 8, is covered by a transparent region 38 configured in the lid wall 8, is preferably provided in the associated portion of the housing wall 5, preferably associated with the rounded transition region of the slot guide 35 to the guide portion 36. The user is provided with a view of the strip 29 guided in the slot guide 35 through the transparent window thus formed, in particular to collect preferably numerical information.

Thus, a number is preferably associated with each chamber 32 on the side of the base strip 30 facing the elevation, said number informing the user how many filled chambers 32 are still available to output the medication M or alternatively how many chambers 32 have already been used as a result of the output of the medication M.

Substantially vertically below the engage-through slot 25 in the housing wall 5, the wall limiting the guide strip 36 on the closure strip side is interrupted to form a fall-through opening 39.

The first edge of the fall-through opening 39, proceeding from the slot guide 35, forms a deflection edge 40, around which the closure strip 31 now released from the base strip 30 of the strip 29 is guided.

The guidance is selected here in such a way that the sharp bending of the closure strip 31 is achieved, preferably while enclosing an acute angle between the region of the closure strip 31, which still adheres to the base strip 30 in front of the deflection edge 40, and the portion of the closure strip 31 guided directly behind the deflection edge 40 of about 15 to 45°, further about 30°.

The closure strip 31 released from the base strip 30 is guided into a closure strip winding cavity 41. The end of the closure strip 31, which is free in this regard, is preferably fixed on a rotationally drivable mandrel 42, around which mandrel 42 the closure strip 31 is gradually wound-on in the course of the rotating drive. The winding-on direction (arrow a) is directed in an opposing manner to the winding-off direction of the strip 29 in the winding chamber 33.

The rotational axis x of the mandrel 42 preferably simultaneously forms the radius axis here for the upper, rounded region of the housing wall 5 and lid wall 8, the deflection edge 40 and the fall-through opening 39 adjacent thereto further being arranged on a radius line passing through the engage-through slot 25, proceeding from the rotational axis x.

The closure strip winding cavity 41 extends to the side of and above the winding chamber 33.

FIG. 8a shows an alternative configuration, in particular regarding the cross-section of the housing, more particularly regarding the guidance of the closure strip 31 in the mounting position of the device 1. A defining portion of the closure strip 31 which extends over the first chamber 32 in the movement direction r is inserted, pushing through a slot of the mandrel 42 preferably arranged diametrically to the rotational axis, such that the fan-like free end 70 of said defining portion extends into a chamber 71 formed between the winding chamber 33 and the closure strip winding cavity 41. During actuation of the rotary handle, if necessary over the course of several inhalation processes, the free fan portion of the closure strip 31 is successively drawn out of the chamber 71, the fan-like portion initially being enveloped in a double layer or subsequently wrapped by subsequent regions of the closure strip 31.

The base strip 30 freed from the closure strip 31 is guided in a prolongation of the guide portion 36, preferably passing thereafter into a section of a circle-like guide region directed downwardly in the shape of a section of a circle and toward the housing centre, which guide region opens freely in an insertion chamber 43.

This insertion chamber 43 preferably extends both to the side of the closure strip winding cavity 41 and also to the side of and partially below the winding chamber 33. Accordingly, the mandrel 42 and the closure strip winding cavity 41 receiving the mandrel 42 are arranged substantially between the winding chamber 33 and the insertion chamber 43.

The base strip 30 is inserted in the insertion chamber 43, a preferably ramp-like introduction portion 44 at the end face bringing about an insertion of the base strip 30 in the direction of the housing centre.

With an increasing length of the strip 39 inserted into the insertion chamber 43, said strip is placed preferably in the manner of a stack in the insertion chamber 43.

The fall-through opening 39 passes below the guide portion 36 into the output region 14, which is substantially encompassed by a wall 45 extending perpendicular to the plane of the housing base 4. A part region of the wall 45 is preferably replaced by the portion of the closure strip 31 guided and preferably clamped between the deflection edge 40 and the wall 45. Further, the wall 45—as described above—has the fall-through opening 39 passing through it.

In the base region of the wall 45, facing the closure strip 31 guided along the wall 45 on the outside of the wall, the wall 45 preferably forms a trough-like portion 46 substantially opening upward in the direction of the fall-through opening 39. The flow channel 13 of the funnel 11 preferably opens into this trough-like portion.

An inflow chamber 47, into which the inflow opening 17 opens in the region of the lid wall 8, is preferably provided above the output region 14 further above the guide portion 36.

The inflow chamber 47 is preferably connected to the output region 14 by means of a flow channel portion 48 configured plane-offset in the width direction of the housing 2. The flow channel portion 48 preferably opens in an end region remote from the trough-like portion 46 of the output region 14.

The space forming the output region 14 is divided by a flap 49 extending substantially diagonally in this space, thus in particular in a flap closure position, to separate the region connected to the flow channel portion 48 and the region extending below the fall-through opening 39.

The flap 49 is preferably configured in the manner of a sealing cloth, more preferably produced from a rubber-like, resiliently restorable material.

The flap 49 substantially has an arm 50 that can be resiliently bent out and which further extends substantially at an acute angle of about 45° in relation to a vertical passing through the housing 2 and the mouth nozzle 10 in an uninfluenced basic position according to FIGS. 8 to 11.

The arm 50 is preferably bound on the foot side in the region of the base-side wall 45 in the output region 14. A sealing portion 51 is formed on the arm 50 opposing this binding region. Said sealing portion extends in a perpendicular section at an obtuse angle to the arm 50, more preferably in the uninfluenced basic position preferably parallel to the base-side wall 45 of the output region 14.

The sealing portion 51 preferably carries an engagement continuation 52 protruding upward in relation to the views in FIGS. 8 to 11, to engage in the uninfluenced position of the flap 49 in the fall-through opening 39.

The flap 49 preferably extends over the entire width of the output region 14 with reference perpendicular to the viewing plane in FIGS. 8 to 11. The vertical thickness of the engagement continuation 52, further viewed in relation to the views, preferably corresponds to the material thickness of the wall of the guide portion 36 limiting the fall-through opening 39.

A rotary handle 53 is further part of the device 1. It is preferably a disc-like or plate-like element with a circular periphery. The rotary handle 53 is preferably arranged associated with the outwardly pointing face of the housing base 4.

The mandrel 42 is formed centrally, i.e. receiving the rotational axis of the rotary handle 53, on the inside of the wall of the rotary handle 53, said mandrel, passing through the housing base 4 in the region of the opening 54, entering the housing interior and, as described above, passing through the closure strip winding cavity 41 here. The mandrel 42 is guided here, as is also correspondingly the rotary handle 53 thereby, preferably by means of a journal 56, which is formed on the inside of the housing of the housing cover 7 and enters a facing end opening 55 of the mandrel 42.

The rotary handle 53 preferably has a radius adapted to the radius of curvature of the housing wall 5 or lid wall 8 in the region of the mouth nozzle 10.

The peripheral edge region of the rotary handle 53 is favourable to handle as a result of the configuration of gripping troughs 57 provided over the periphery.

The rotary handle 53 is substantially a part of a stepping mechanism for the step-wise further guidance of the strip 29. For this purpose, a peripheral sprocket wheel 58, preferably oriented radially inward, is firstly provided on the inside of the wall of the peripheral edge of the rotary handle 53 having the gripping troughs 57. The teeth of the sprocket wheel 58 are preferably set in a saw tooth-like manner in the predetermined rotational direction of the rotary handle 53 according to the arrow a.

The sprocket wheel 58 preferably continues into a toothed ring 59, which is formed on the face of the rotary handle 53 facing the housing base 4, the teeth of which accordingly preferably point in the axial direction of the rotary handle 53.

A further toothed ring 60 that is reduced in diameter in relation to the sprocket wheel 58 is worked in concentrically to the sprocket wheel 58 on the inside of the rotary handle 53, i.e. on the handle face facing the housing base 4. This toothed ring 60 is formed substantially in the manner of a serration.

A blocking tooth 61, which is preferably formed in the region of the housing base 4 and is resiliently resettable, engages in the toothed ring 60. Its cooperation region with the toothed ring 60 is configured in such a way that said toothed ring merely allows rotation of the rotary handle 53 in the predetermined rotational direction according to the arrow a, but prevents rotation of the rotary handle 53 counter to the arrow direction a as a result of blocking.

The toothed ring 58 is preferably used for cooperation with a blocking element 62 pivotally mounted in the housing 2 about a pivot axis y oriented parallel to the rotational axis x.

This blocking element 62 is preferably arranged in a blocking element chamber 63 formed, in relation to the views above the guide portion 36, in the movement direction r of the strip 29 substantially in front of the fall-through opening 39, this being substantially below the mouth nozzle 10.

The opening 15 opening at the other end toward the mouth nozzle 10 simultaneously opens into this blocking element chamber 63.

The blocking element 62 preferably firstly has a hub 64, which is pivotally movably seated on an axial body 65 preferably formed on the housing part 3 on the inside of the wall of the housing base 4.

An arm, which, at the end carries an engagement tooth 66 pointing upward in the direction of the mouth nozzle 10 in the views, protrudes substantially radially outwardly from this hub 64.

The engagement tooth 66 is preferably lengthened perpendicular to the plane of viewing, for example of FIG. 8, over the width of the housing 2 in the direction of the rotary handle 53, thus passing through a window-like aperture 67 in the housing base 4, for engagement in the toothed ring 59 of the handle 53.

Furthermore, a curved spring arm 68, the free end of which pointing downward in the direction of the strip 29 forms a straight sensing finger 69, is formed on the hub 64, preferably substantially diametrically opposing the arm carrying the engagement tooth 66.

The functioning of the device 1 is as follows:

In the situation shown in FIG. 8 before first use of the device 1, the strip 29 is placed in the housing 2 in such a way that, proceeding from the strip winding in the winding chamber 33, the strip extends by way of the slot guide 35 and the guide portion 36 at least until it overlaps the blocking element chamber 63.

A portion of the closure strip 31 protruding beyond the first chamber 32 of the base strip 29 in the movement direction r is placed about the deflection edge 40 and fixed on the mandrel 42, while a portion of the base strip 30 in this regard extends substantially in prolongation of the extent of the strip in the guide portion 36, bridging the fall-through opening 39, further in the direction of the insertion chamber 43.

To prepare, in particular, an inhalation process, the mouth closure cap 18 is firstly pulled off the mouth nozzle 10 and thereafter deposited laterally on the housing 2, preferably as a result of pivoting.

Thereafter, the mandrel 42 is rotated in the predetermined rotational direction according to the arrow a by means of the rotary handle 53.

The sensing finger 69 of the blocking element 62, which, in the course of rotation in the intermediate space, viewed in the movement direction r, firstly engages between two chambers 32 located one behind the other, is acted upon by the following raised chamber 32 during the further rotational displacement and accompanying displacement of the strip 29, in particular in the guide portion 36, said guide portion as a result of pulling displacement by means of the closure strip 31 winding around the mandrel 42. As a result of the corresponding support of the sensing finger 69 on the associated chamber 32, this leads to a pivoting displacement of the entire blocking element 62 into a position, in which the engagement tooth 66 of the blocking element 62 engages in a blocking manner in the sprocket wheel 58 of the rotary handle 53. The rotary handle 53 is accordingly no longer rotationally displaceable in this position. The rotary displacement in the predetermined direction according to arrow a is blocked by the blocking element 62 with virtually no rotational force being applied to the chamber 32. The rotary displacement in the opposite direction is blocked by the blocking tooth 61.

The blocking of the rotary handle 53 gives the user the signal that the device 1 is now ready for the portioned output of the medication M, in particular for its inhalation.

The chamber 32 arranged upstream in the movement direction r of the chamber 32 cooperating with the sensing finger 69 of the blocking element 62, in this position, lies above the fall-through opening 39 and is moreover freed from the closure strip 31 as a result of pulling off about the deflection edge 40. Accordingly, the chamber 32 associated with the fall-through opening 39 is opened downwardly—in relation to the views.

The medication M in this chamber 32 is, however, firstly secured against trickling out by the flap 49 staying in the closure position, in which the engagement continuation 32 thereof, engaging in the fall-through opening 39, firstly closes the associated chamber 32.

This at the same time also prevents double dosing when the user, in this device position, decides to not carry out the inhalation process. The resetting and reactivation of the system—as described in more detail below—indeed leads to the corresponding provision of the next chamber 32. The previously opened and provided chamber 32 is displaced here, still containing the medication M, in the direction of the insertion chamber 43, the chamber opening being covered during this further insertion displacement, by the facing wall of the guide portion 36 at the bottom. The trickling out of the medication M placed in the opened chamber 32 is preferably firstly achieved in the region of the insertion chamber 43, therefore, accordingly, in a flow region not being used for the purpose of inhalation.

For the purpose of inhalation, the mouth nozzle 10 is encompassed by the user's lips. As a result of breathing in deeply, a suction air flow (arrow c) is produced, which, in the region associated with the portion 46 of the output region 14, firstly produces a negative pressure, which leads to the starting of the pivoting of the flap 49 into a position freeing the fall-through opening 39, this being counter to the restoring spring force of the flap 49.

With the pivoting in of the flap 49, the flow path to the flow channel portion 48 is freed, whereupon, with the suction air then starting up and sucked in via the inflow opening 17, the flap 49 is optionally further displaced counter to the restoring force.

By means of the displaced flap 49, the opening of the closure strip-free chamber 32 associated with the fall-through opening 39 is freed to output the medication M. This is cleared, optionally while superimposing a trickling out of the chamber 32, from the chamber 32 by the suction air, more preferably swirled, in particular in the region of the portion 46 of the output region 14, for preferred uniform distribution in the suction air and thereafter discharged via the flow channel 13, the funnel 11 and the mouth nozzle 10, for inhalation.

Upon the ending of the inhalation process and therefore the breaking off of the suction air flow, the flap 49 automatically falls back as a result of the provided restoring force into the position closing the fall-through opening 39 again.

In conclusion, the mouth closure cap 18 is placed on the mouth nozzle 10, the cap-side projections 27 and 28 passing through the corresponding through-openings 15 and 16, the inflow opening 17 further, in particular, being covered by means of the guide portion 21 of the mouth closure cap 18, this, in particular, to prevent the entry of dirt or the like when the device 1 is not in use.

The projection 27 passing through the through-opening 15 acts, while the closure cap 18 is being placed on the mouth nozzle 10, on the engagement tooth 66 of the blocking element 62, in such a way that the pivoting displacement of the blocking element 62 into a disengagement position with respect to the sprocket wheel 58 is achieved thereby.

During this pivoting movement, the sensing finger 69, as a result of the resilient configuration of the spring arm 68, slides over the chamber 32 bringing about the blocking in the process previously carried out, and thereafter enters the intermediate space left behind this chamber in the movement direction r between this chamber 32 and the subsequent chamber 32 in the movement direction r. The blocking element 62 is accordingly brought back again into a stand-by position for sensing the next chamber 32 during the next displacement process.

The rotary blocking of the rotary handle 53, which is firstly cancelled as a result of the displacement of the blocking element 62, is taken on in this mouth nozzle closure position by the further projection 28, which, passing through the through-opening 16 in a blocking manner, engages in the toothed ring 59 of the rotary handle 53.

In a preferred and also shown configuration, the chamber 32 blocking the blocking element 62 in the blocking position of the rotary handle 53 after the resetting of the system as a result of the placing of the closure cap 18 is the chamber from which medication M will be offered for release at the next actuation of the rotary handle.

During the individual outputs of medication portions or during the individual consecutive inhalations, the closure strip 31 is successively wound-on to the mandrel 42, while the base strip 30 substantially provided with emptied chambers 32 is successively inserted into the insertion chamber 43, in which the base strip 30 is gradually deposited substantially in a stack-like manner.

The displacement path of the strip 29, for each actuation of the rotary handle, as a result of the proposed solution, is solely dependent on the spacing of the chambers 32 from one another and furthermore derived from this spacing. The rotation angle of the rotary handle 53 reduces in the course of the increase in the winding diameter on the mandrel 42, thus preferably proceeding from 90° to a reduced rotation angle of about 70° to 85°, more preferably about 80°.

Figure 15:
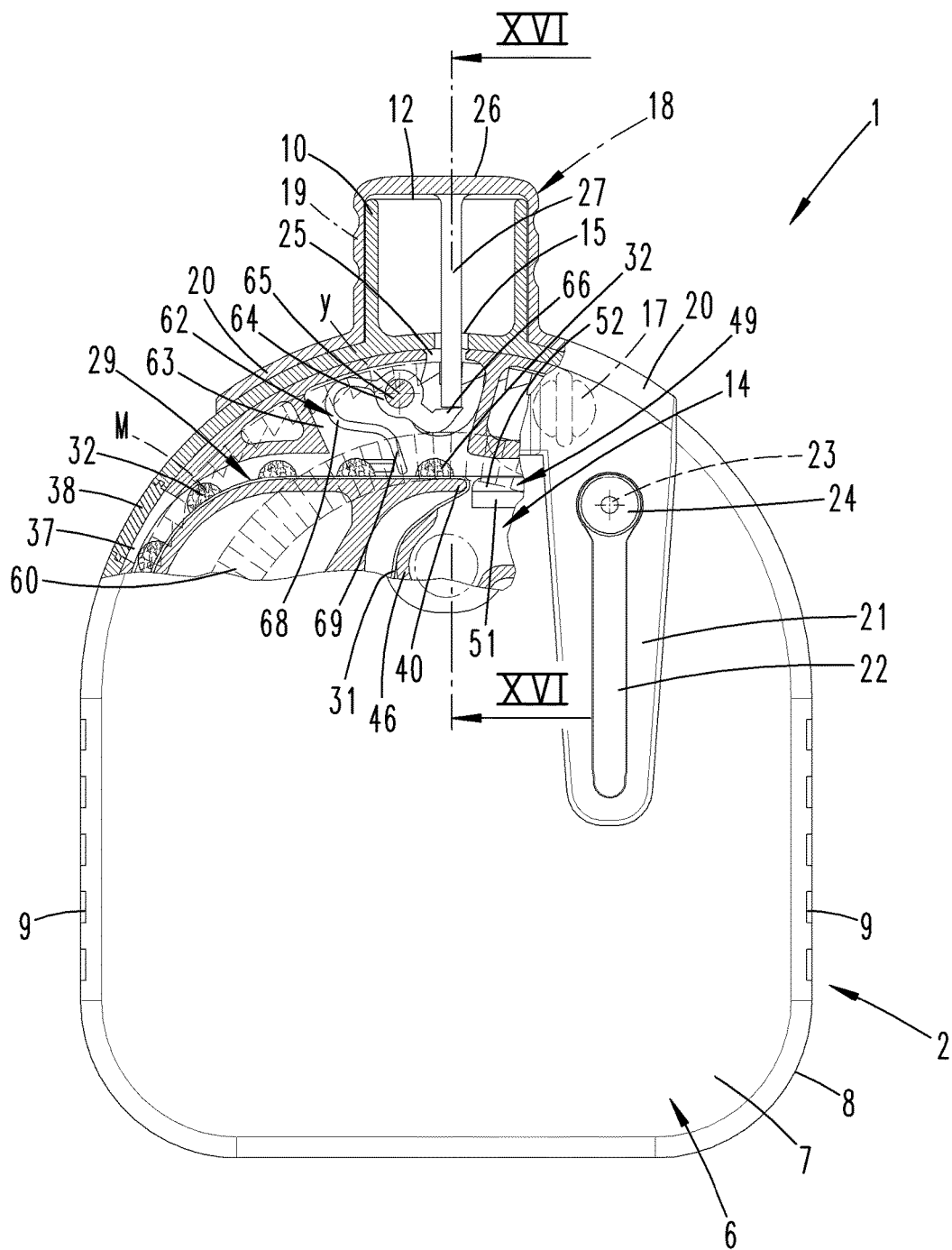
FIG. 15 shows a view corresponding to FIG. 11, relating to the cap placing position.
Figure 16:
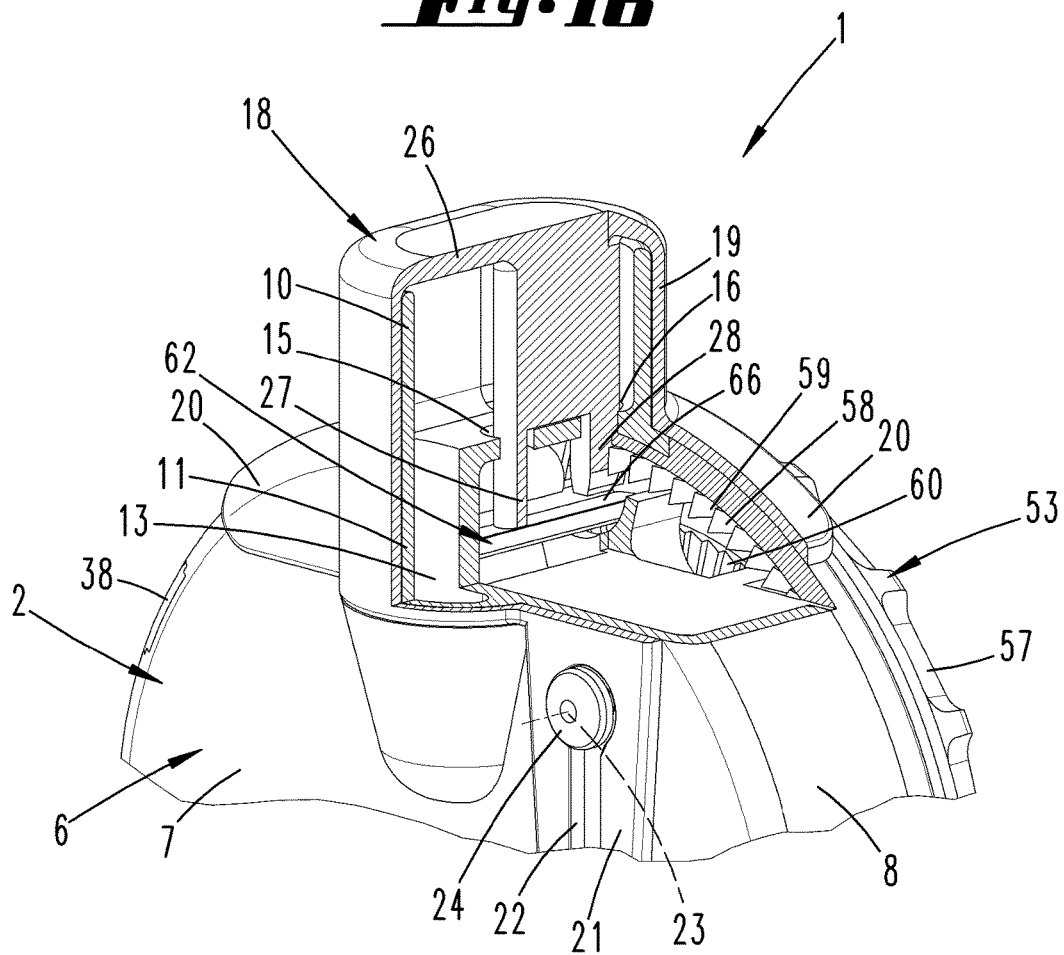
FIG. 16 shows the section along the line XVI-XVI in FIG. 15.

The position shown in FIG. 15 preferably corresponds to the delivery state of the device 1, i.e. more preferably to the state before the device is first used by the user.

The strip 29 comprising the chambers 32 is preferably inserted in the device 1 by the manufacturer and is transported in the movement direction r by rotating the rotary handle 53 until the first chamber 32 in the movement direction r displaces the blocking element 62 into the position blocking the rotary handle 53. Upon the final placing of the mouth closure cap 18, the blocking element 62 is pivotally displaced into the position shown in FIG. 15, in which position the sensing finger 69 enters a region between the first chamber and the second chamber 32 viewed in the movement direction. The rotary handle 53 is consequently ready for a first use by the user once the cap has been removed. The handling of the device 1 is the same for the first use as for each subsequent use.

In the first use position according to FIG. 15, the first chamber 32 viewed in the movement direction is located at a distance in front of the deflection edge 40, more particularly at a distance from the fall-through opening 39. Accordingly, the sealing closure of the first chamber 32 is provided by the closure strip 31, as is also the case in each subsequent preparation position upon placing the cap onto the mouth piece in each subsequent chamber 32 to be freed for the next inhalation.

The distance between two consecutive chambers 32 viewed in the movement direction r is selected such that, upon displacement of the blocking element into the blocking position 62 by a subsequent chamber 32 which frees the chamber 32 in front of the chamber actuating the blocking element in the movement direction r from the closure strip 31 is positioned above the fall-through opening 39 closed by the flap.

All the features disclosed are essential to the invention (per se). The disclosure content of the associated/accompanying priority documents (copy of the prior application) is also included herein in its entirety in the disclosure of the application, including for the purpose of also adopting features of these documents in claims of the present application. The sub-claims characterise independent inventive developments of the prior art in their optionally coordinated version, in particular in order to make provisional applications on the basis of these claims.

LIST OF REFERENCE NUMERALS

1 device
2 housing
3 housing part
4 housing base
5 housing wall
6 housing lid
7 housing cover
8 lid wall
9 gripping zone
10 mouth nozzle
11 funnel
12 mouth opening
13 flow channel
14 output region
15 through-opening
16 through-opening
17 inflow opening
18 mouth closure cap
19 slip-over portion
20 portion
21 guide portion
22 recess
23 journal
24 radial collar
25 engage-through slot
26 cap cover
27 projection
28 projection
29 strip
30 base strip
31 closure strip
32 chamber
33 winding chamber
34 winding chamber wall 35 slot guide
36 introduction portion
37 aperture
38 transparent region
39 fall-through opening
40 deflection edge
41 closure strip winding cavity
42 mandrel
43 insertion chamber
44 guide portion
45 wall
46 portion
47 inflow chamber
48 flow channel portion
49 flap
50 arm
51 sealing portion
52 engagement continuation
53 rotary handle
54 opening
55 end opening
56 journal
57 gripping trough
58 sprocket wheel
59 toothed ring
60 toothed ring
61 blocking tooth
62 blocking element
63 blocking element chamber
64 hub
65 axial body
66 engagement tooth
67 opening
68 spring arm
69 sensing finger
70 free end
71 chamber
M medication
a arrow
b width
h height
c arrow
r movement direction
t depth
x rotational axis
y pivot axis

The invention claimed is:

1. Device for portioned output of medication from individual chambers of a strip, the individual chambers being arranged one behind another, the strip comprising a base strip and a closure strip, the individual chambers of the strip being raised,
    wherein the individual chambers can be opened by actuating a handle by sharply deflecting the closure strip,
    wherein in a blocking position a chamber elevation directed towards a mouth piece opening blocks the actuation of the handle via a blocking element,
    wherein in the blocking position a chamber arranged upstream of the chamber elevation in terms of movement and freed of the closure strip is located above a fall-through opening,
    wherein the fall-through opening is closed via a flap, and
    wherein the flap can be moved into an open position via a suction air stream.

2. Device according to claim 1, wherein an initial stop position of the closure strip is before a front chamber reaches a deflection edge and before a subsequent chamber reaches the blocking element.

3. Device according to claim 1, wherein the blocking element has two arms.

4. Device according to claim 1, wherein the strip has closed chambers and is wound-on in a winding chamber,
    wherein the chamber elevation faces outward, and
    wherein the base strip continuing beyond a deflection point extends into an enlarged insertion chamber, while the closure strip is wound-on on a mandrel driven by the handle which is a rotary handle.

5. Device according to claim 4, wherein the blocking element, the fall-through opening and the mandrel are located one behind another on a radial of the rotary handle.

6. Device according to claim 4, wherein an introduction portion predetermining an insertion direction of the base strip into an introduction chamber is configured upstream of the insertion chamber in a movement direction of the base strip.

7. Device according to claim 4, wherein a serration on a back of the rotary handle has a sprocket wheel on an inside for engagement with an engagement tooth such that, when the rotary handle is stopped, a retention force is directed towards a pivot axis of the blocking element.

8. Device according to claim 1, wherein, in the blocking position, the blocking element exerts virtually no torque on the chamber elevation.

9. Device according to claim 1, wherein the blocking element can be returned by a projection of a mouth closure cap into a preparation position, to sense the next chamber.

10. Device according to claim 9, wherein the mouth closure cap can be longitudinally, displaceably and pivotally placed on a mouth nozzle.

11. Device according to claim 9, wherein a rotary projection of the mouth closure cap is arranged as a blocking part of the handle which is a rotary handle.

12. Device according to claim 1, wherein the handle is a rotary handle is arranged in a partly overlapping manner in front of a side wall of a housing as a disc having a surface area.

13. Device according to claim 1, wherein the fall-through opening for suction air discharge of the medication leads to the mouth piece opening, and
    wherein the mouth piece opening can be closed by a lid.

* * * * *

UNITED STATES PATENT AND TRADEMARK OFFICE
CERTIFICATE OF CORRECTION

PATENT NO. : 9,956,361 B2  
APPLICATION NO. : 14/386283  
DATED : May 1, 2018  
INVENTOR(S) : Von Schuckmann It is certified that error appears in the above-identified patent and that said Letters Patent is hereby corrected as shown below:

In the Claims

In Column 16, Line 49, (Line 2 of Claim 12) after "handle" please delete the word: "is".

Signed and Sealed this  
Fifth Day of June, 2018

Andrei Iancu  
*Director of the United States Patent and Trademark Office*